(12) United States Patent
Haraguchi et al.

(10) Patent No.: US 11,504,199 B2
(45) Date of Patent: Nov. 22, 2022

(54) MEDICAL MANIPULATOR

(71) Applicant: OLYMPUS CORPORATION, Tokyo (JP)

(72) Inventors: Masafumi Haraguchi, Tokyo (JP); Shintaro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 252 days.

(21) Appl. No.: 17/005,688

(22) Filed: Aug. 28, 2020

(65) Prior Publication Data
US 2020/0390508 A1 Dec. 17, 2020

Related U.S. Application Data

(60) Division of application No. 15/816,418, filed on Nov. 17, 2017, now Pat. No. 10,792,116, which is a
(Continued)

(30) Foreign Application Priority Data

May 27, 2015 (JP) .............................. JP2015-106996

(51) Int. Cl.
*A61B 34/00* (2016.01)
*A61B 1/005* (2006.01)
(Continued)

(52) U.S. Cl.
CPC ............ *A61B 34/71* (2016.02); *A61B 1/0016* (2013.01); *A61B 1/0052* (2013.01);
(Continued)

(58) Field of Classification Search
CPC .... A61B 1/0016; A61B 1/0052; A61B 1/0057
See application file for complete search history.

(56) References Cited

U.S. PATENT DOCUMENTS

| 4,499,895 A | 2/1985 | Takayama |
| 2004/0073084 A1* | 4/2004 | Maeda ............... A61B 1/00042 600/101 |

(Continued)

FOREIGN PATENT DOCUMENTS

| JP | S51-91990 U1 | 7/1976 |
| JP | S55-54481 Y2 | 12/1980 |

(Continued)

OTHER PUBLICATIONS

International Search Report dated Aug. 9, 2016 received in PCT/JP2016/065140.
(Continued)

*Primary Examiner* — Aaron B Fairchild
(74) *Attorney, Agent, or Firm* — Scully, Scott, Murphy & Presser, P.C.

(57) ABSTRACT

A medical manipulator including an insertion portion, where the insertion section including a bending portion and an end effector disposed on a distal end side of the insertion portion. The medical manipulator further including an actuator configured to generate a first drive force for moving the bending portion; a lever configured to generate a second drive force for moving the bending portion, the lever being used to move the bending portion instead of the actuator; a wire configured to transmit the first drive force or the second drive force to the bending portion; and a transmission blocking device configured to switch from the first drive force to the second drive force.

15 Claims, 5 Drawing Sheets

Related U.S. Application Data continuation of application No. PCT/JP2016/065140, filed on May 23, 2016.

(51) Int. Cl.
  *A61B 1/00* (2006.01)
  *A61B 90/00* (2016.01)
  *A61B 1/05* (2006.01)
  *A61B 1/06* (2006.01)

(52) U.S. Cl.
  CPC .......... *A61B 1/0057* (2013.01); *A61B 1/0055* (2013.01); *A61B 1/00087* (2013.01); *A61B 1/00096* (2013.01); *A61B 1/05* (2013.01); *A61B 1/0684* (2013.01); *A61B 2090/034* (2016.02)

(56) References Cited

U.S. PATENT DOCUMENTS

| | | | |
|---|---|---|---|
| 2008/0312503 A1 | 12/2008 | Masaki | |
| 2009/0076330 A1* | 3/2009 | Ashida | A61B 1/00042 600/146 |
| 2013/0047757 A1 | 2/2013 | Okamoto et al. | |
| 2015/0105615 A1 | 4/2015 | Kato | |

FOREIGN PATENT DOCUMENTS

| | | |
|---|---|---|
| JP | H04-241829 A | 8/1992 |
| JP | H05-49594 A | 3/1993 |
| JP | 2002-125919 A | 5/2002 |
| JP | 2003-070727 A | 3/2003 |
| JP | 2005-323662 A | 11/2005 |
| JP | 4722245 B2 | 7/2011 |
| JP | 2013-215238 A | 10/2013 |

OTHER PUBLICATIONS

Japanese Office Action (Notice of Allowance) dated May 16, 2017 received in 2017-513277.
Extended Supplementary European Search Report dated Jan. 21, 2019 in European Patent Application No. 16 79 9978.8.
Office Action dated Apr. 3, 2020 received in U.S. Appl. No. 15/816,418.

* cited by examiner

MEDICAL MANIPULATOR

CROSS-REFERENCE TO RELATED APPLICATIONS

This application is a Divisional Application of U.S. application Ser. No. 15/816,418, filed on Nov. 17, 2017, which is a continuation application based on a PCT International Application No. PCT 2016/065140, filed on May 23, 2016, which claims priority to Japanese Patent Application No. 2015-106996, filed on May 27, 2015, the contents of each of which are incorporated herein by reference.

BACKGROUND

Field

The present disclosure relates to a medical manipulator.

Prior Art

In laparoscopic surgery, it is necessary to observe and treat an affected area through a limited access route. Therefore, compared with laparotomy surgery, the degrees of freedom are limited and the difficulty of a procedure is high, but the benefits to patients are large in view of postsurgical recovery.

In the laparoscopic surgery, observation and treatment with high degrees of freedom is possible by using a medical manipulator having a bending mechanism at a distal end thereof. Control of a drive system corresponding to a motion of an operator's hand is required to intuitively handle the bending mechanism with high degrees of freedom.

By using an electric control technology, desired performance can be obtained, but a bending portion which is inserted into a body may also be fixed in a bent state due to failure in the drive system or the like. If the bent state of the bending portion is fixed, the patient may be burdened when the medical manipulator is removed from the patient. Therefore, a countermeasure which is designed to avoid the fixed state of the bending mechanism even when a problem occurs is required.

In order to release fixing of the bent state, Japanese Patent No. 4722245 has proposed to provide a power transmission blocking mechanism such as a clutch in a power transmission mechanism. After the power transmission blocking mechanism is activated, a manual operation handle is attached, and a chain driven by a motor or the like is manually operated.

SUMMARY

Accordingly, a medical manipulator is provided. The medical manipulator comprising: an insertion portion comprising: a bending portion; and an end effector disposed on a distal end side of the insertion portion; a motor configured to generate a first drive force for moving the bending portion; a lever configured to generate a second drive force for moving the bending portion, the lever being used to move the bending portion instead of the motor; a wire configured to transmit the first drive force or the second drive force to the bending portion; and a transmission blocking device configured to switch from the first drive force to the second drive force, the transmission blocking device comprises a cutting surface, the cutting surface being configured to cut a portion of the wire located between the motor and the lever.

The lever can comprise a handle configured to generate the second drive force when the handle is moved from a first position to a second position.

Also provided is a medical manipulator including: an insertion portion comprising: a bending portion; and an end effector disposed on a distal end side of the insertion portion; a motor configured to generate a first drive force for moving the bending portion; a lever configured to generate a second drive force for moving the bending portion, the lever being used to move the bending portion instead of the motor; a wire configured to transmit the first drive force or the second drive force to the bending portion; and a transmission blocking device configured to switch from the first drive force to the second drive force, the transmission blocking device being configured to produce slack in a portion of the wire between the motor and the lever.

DETAILED DESCRIPTION

Hereinafter, a first embodiment will be described with reference to FIGS. 1 to 3.

Figure 1:
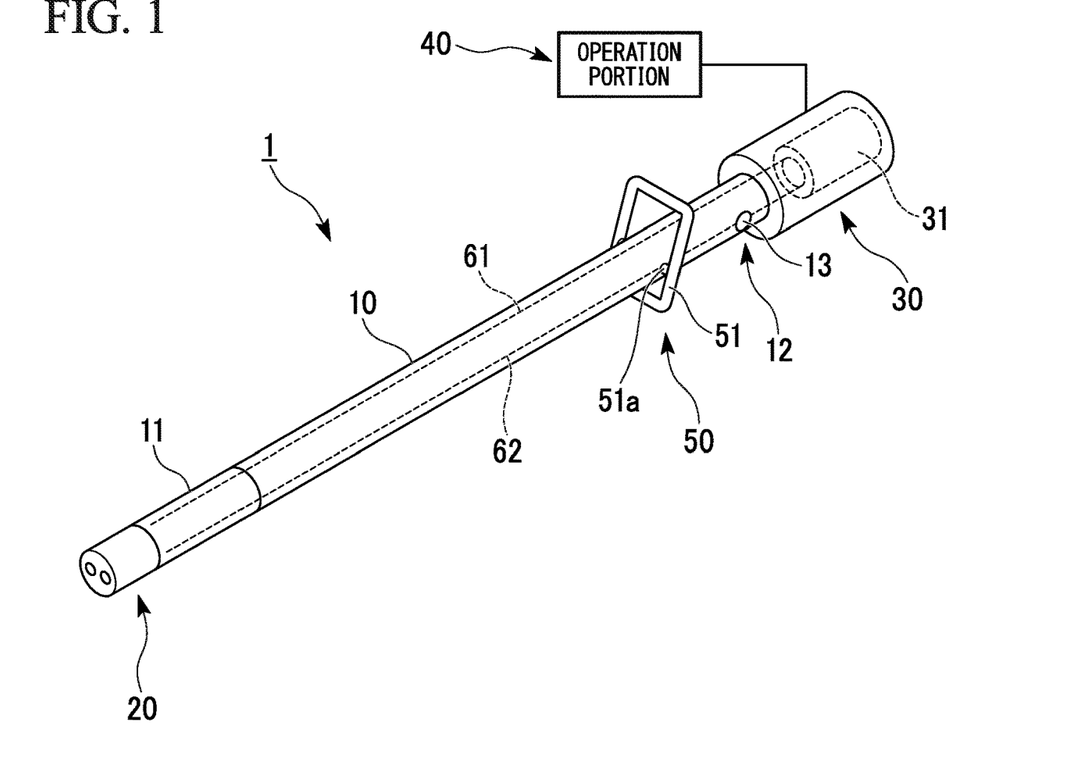
FIG. 1 is an overall view of an endoscope according to a first embodiment.

FIG. 1 is an overall view of an endoscope 1 which is a medical manipulator according to the present embodiment. The endoscope 1 is inserted into a body cavity through a trocar or the like when used in laparoscopic surgery or the like. The endoscope 1 includes an insertion portion 10, an observation portion (end effector) 20, a first drive portion 30 (a lever having mechanical advantage) and an operation portion 40. The insertion portion 10 has a bending portion 11 capable of performing a bending operation on a distal end side of the insertion portion 10. The observation portion 20 is attached at a distal end of the insertion portion 10. The first drive portion 30 is attached at a proximal end of the insertion portion 10. The operation portion 40 is provided for operating the first drive portion 30.

The insertion portion 10 is formed from a metal or the like in a cylindrical shape. The bending portion 11 has a known structure in which a plurality of joint rings or bending frames (which may be referred to hereinafter as "joint rings, or the like") are disposed side by side in an axial direction. The joint ring or the like on the distal end and the first drive portion 30 are connected by a pair of wires (power transmission members) 61 and 62. The pair of wires 61 and 62 are inserted through the insertion portion 10. An operation of bending the bending portion 11 can be performed by advancing and retracting the wires 61 and 62 by a drive force generated from the first drive portion 30.

The observation portion 20 has a known structure including an imaging part and an illumination part. The imaging part is an image sensor having a solid-state imaging device or the like, such as a CCD or CMOS. The illumination part has a light emitting diode (LED), a light guide connected to a light source or the like. An image acquired by the observation portion 20 is displayed on an external monitor or the like, which is not shown, and the observation portion 20 is connected to the endoscope 1 through a wiring or the like passing through the insertion portion 10.

The first drive portion 30 includes a drive mechanism 31 such as a motor which generates a drive force. The drive mechanism 31 is connected to the wires 61 and 62 to transmit the generated drive force. The drive mechanism 31 and the wires 61 and 62 may be directly connected or may be connected via a gear or the like disposed for deceleration.

The operation portion 40 is not limited particularly to a specific configuration or installation position as long as it can operate the drive mechanism 31, and a known structure or the like may be appropriately selected and used.

A second drive portion 50 is disposed between the bending portion 11 and the first drive portion 30 at a position which is located outside the body when the endoscope 1 is used. The second drive portion 50 is used for operating the bending portion 11 in an emergency state. Although a handle 51 is attached at the second drive portion 50, an operation thereof is not performed by a user in a normal state.

Figure 2:
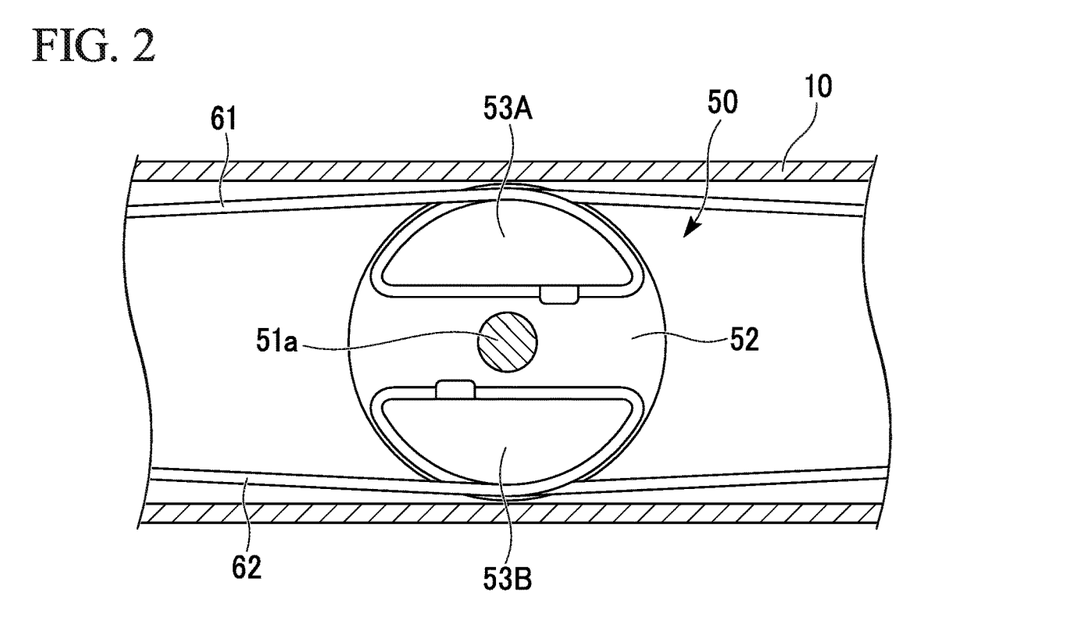
FIG. 2 is a view showing a second drive portion in the endoscope according to the first embodiment.

FIG. 2 is a view showing a cross section of a portion of the insertion portion 10 in which the second drive portion 50 is provided. The second drive portion 50 includes a pulley 52 to which the pair of wires 61 and 62 are connected.

The pulley 52 has a pair of protrusions 53A and 53B having an approximately semicircular cross-sectional shape on one surface thereof in the axial direction. The pair of wires 61 and 62 are respectively wound on the protrusions 53A and 53B, and a part of the wound portion is connected to the pulley 52 by soldering, adhesion, welding or the like.

The handle 51 has a shaft portion 51a extending into the insertion portion 10. The shaft portion 51a is fixed to the pulley 52.

As shown in FIG. 1, a through-hole 12 which communicates with an inside of the insertion portion 10 is provided in a portion of the insertion portion 10 between the second drive portion 50 and the first drive portion 30. Although the through-hole 12 is closed by a cover 13 in the normal state, the cover 13 is removed in the emergency state, and a cutting member which will be described later is inserted therein.

An operation of the endoscope 1 according to the embodiment configured as described above will be described.

In the normal state when the first drive portion 30 is operated normally, the user operates the operation portion 40 to drive the first drive portion 30, and performs the bending operation of the bending portion 11. In the present embodiment, since the pair of wires 61 and 62 are attached at the bending portion 11, the bending operation in two directions can be performed.

In the normal state, the handle 51 of the second drive portion 50 rotates about the shaft portion 51a following the bending operation of the bending portion 11.

In the emergency state in which the drive mechanism 31 of the first drive portion 30 fails or power is not supplied to the drive mechanism 31, the bending portion 11 is fixed in the shape that the bending portion 11 had immediately before the emergency state. When the shape of the bending portion 11 from immediately before the emergency state is a bent state, it is difficult to remove the endoscope 1 from the inserted trocar or the like.

When the emergency state occurs, the user performs a predetermined emergency operation to block transmission of the drive force from the first drive portion 30 to the wires 61 and 62.

The user removes the cover 13 and inserts the cutting member (transmission blocking device) into the through-hole 12.

Figure 3:
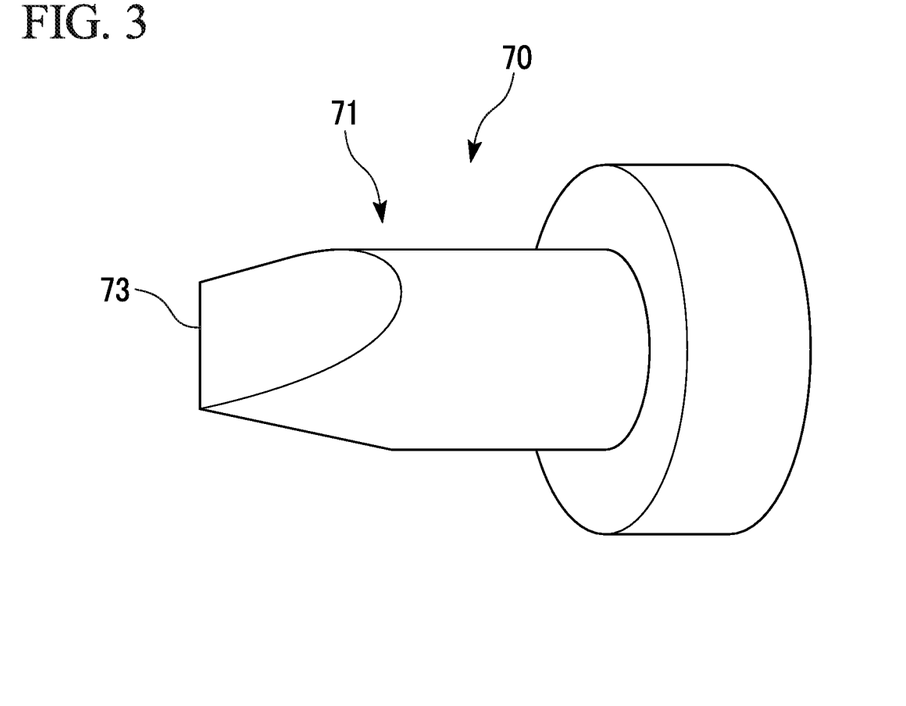
FIG. 3 is a view showing a cutting member in the endoscope according to the first embodiment.

FIG. 3 shows a shape of the cutting member 70. The cutting member 70 has a protruding portion 71 which can be inserted into the through-hole 12. The cutting member includes a surface, such as a cutting blade 73, capable of cutting the wires 61 and 62 is formed at a distal end portion of the protruding portion 71. When the user inserts the protruding portion 71 into the through-hole 12 and presses it, the wires 61 and 62 can be cut by the blade 73.

When the wires 61 and 62 are cut by the cutting member 70, a region of the wires 61 and 62 that is connected to the pulley 52 of the second drive portion 50 and is disposed more distal than the cutting part is in a state in which the region of the wires 61 and 62 is free from interference of the first drive portion 30. Therefore, the user rotates the pulley 52 by rotating the handle 51 such that the wires 61 and 62 connected to the bending portion 11 can advance and retract with respect to the insertion portion 10. As a result, a procedure can be continued even after a problem occurs in the first drive portion 30. Also, since the bending portion 11 can be formed into a straight linear shape by operating the handle 51, a patient is not burdened when the endoscope 1 is removed.

As described above, according to the endoscope 1 according to the embodiment, since the endoscope 1 has the second drive portion 50 and the cutting member 70, even when a problem occurs in the first drive portion 30 and an operation of the bending portion 11 by the first drive portion 30 becomes difficult, the bending portion 11 can be bent using the second drive portion 50 by cutting the wires 61 and 62 with the cutting member 70. Therefore, the procedure or treatment can be continued without introducing another medical manipulator into the patient's body. After the procedure or treatment using the second drive portion 50 is completed, the bending portion 11 can be formed into a straight shape and can be suitably removed without burdening the patient.

Unlike a method in which a clutch or the like is provided in the drive mechanism, even when there is no problem with the drive mechanism but an abnormality in engagement of the gear for deceleration occurs, the bending portion 11 can be reliably bent using the second drive portion 50. Accordingly, regardless of a type of the problem occurring in the first drive portion 30, a manual operation of the bending portion 11 can be reliably performed in the emergency state.

In the embodiment, for example, a key and a key groove may be provided in the through-hole 12 and the protruding portion 71 such that the blade 73 is facing in a direction in which the wire can be reliably cut when the cutting member 70 is inserted.

Next, a second embodiment will be described with reference to FIG. 4 to FIG. 7. The second embodiment is different from the first embodiment in a configuration of the second drive portion. In the following description, the same reference numerals are provided for the configurations which are the same as those already described, and repeated descriptions will be omitted.

Figure 4:
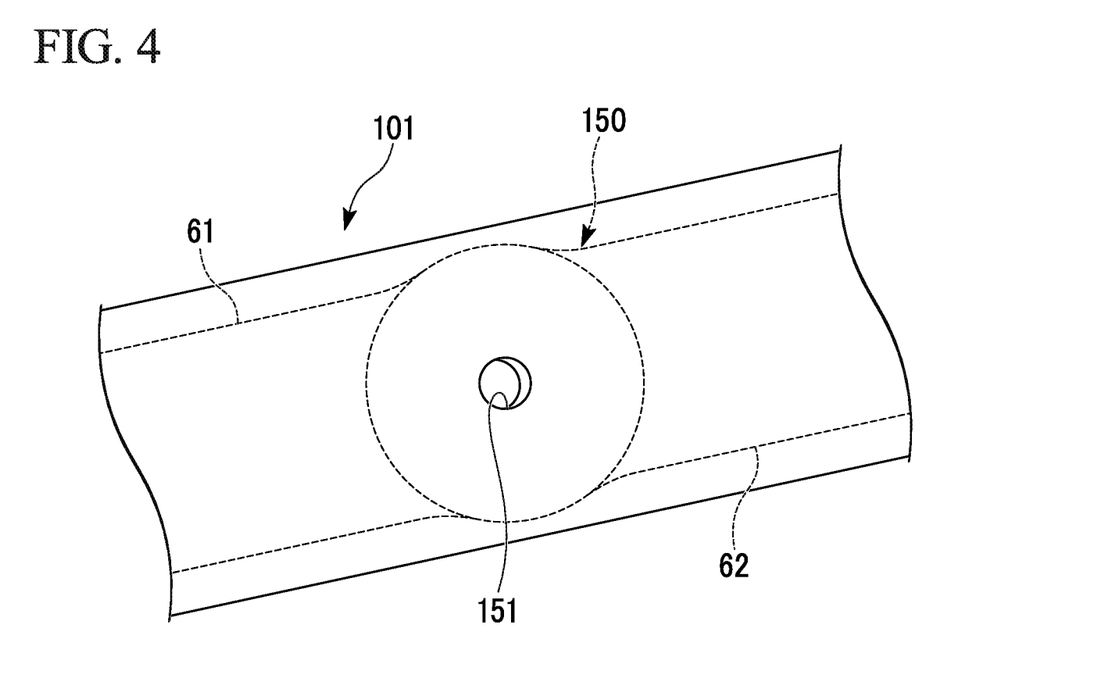
FIG. 4 is a partially enlarged view showing an insertion portion of an endoscope according to a second embodiment.

FIG. 4 is a partially enlarged view showing a portion in which a second drive portion 150 is provided in an endoscope 101 according to the second embodiment. A pair of through-holes 151 into which a handle 51 is inserted in an emergency state are provided in an insertion portion of a portion in which the second drive portion 150 is provided (one of the through-holes 151 is not shown). Like the first embodiment, the pair of through-holes 151 may be closed by a cover or the like in a normal state.

Figure 5:
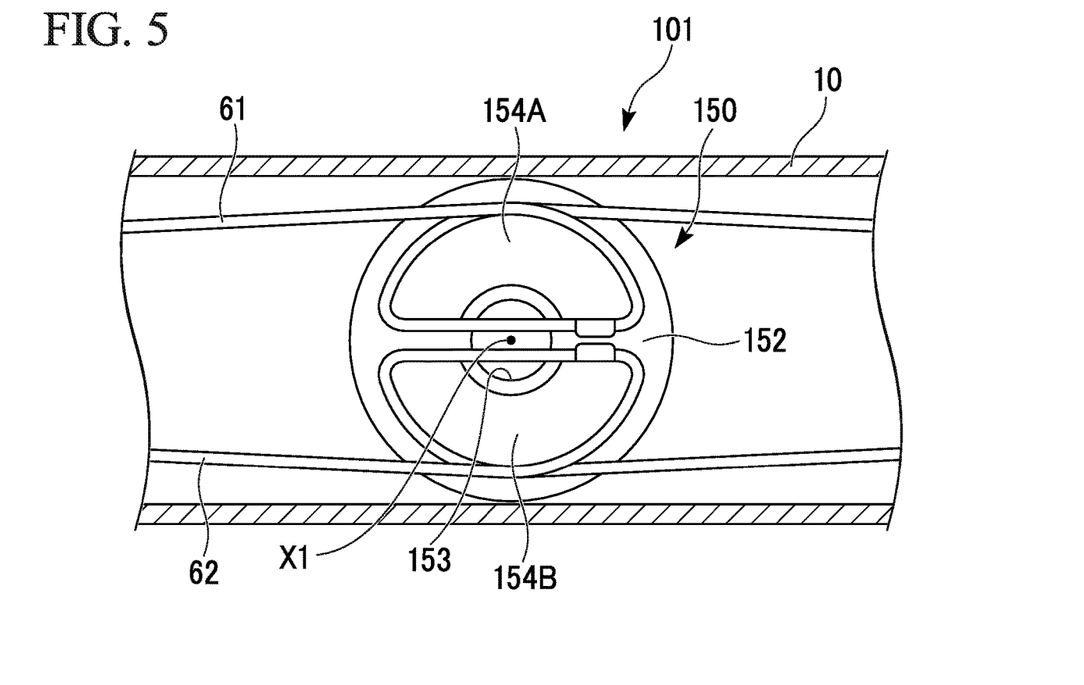
FIG. 5 is a view showing a second drive portion in the endoscope according.

FIG. 5 is a view showing the second drive portion 150 which is accommodated in an insertion portion 10. The second drive portion 150 includes a pulley 152 to which the wires 61 and 62 are connected. The pulley 152 has a shaft hole 153 and two protrusions 154A and 154B. The shaft hole 153 is formed to include a rotation axis X1 and to extend in parallel with the rotation axis X1. The wires 61 and 62 are wound on the protrusions 154A and 154B, respectively. Each of the protrusions 154A and 154B has an approximately semicircular cross section approximately similar to that in the first embodiment, but a part of each of the protrusions 154 A and 154 B overlaps the shaft hole 153 when the pulley 152 is viewed in an extending direction of the rotation axis X1, and the overlapping portion is cut. Therefore, a portion of each of the wires 61 and 62 wound on the protrusions 154A and 154B is disposed to traverse the shaft hole 153. The pulley 152 and the wires 61 and 62 are connected by soldering or the like at a portion located on a distal end side of a portion of the wire which traverses the shaft hole 153.

The pulley 152 having the shaft hole 153 cannot be pivotally supported by the insertion portion 10. For example, by providing a circumferential wall which protrudes from an inner surface of the insertion portion and defines a cylindrical space capable of accommodating the protrusions 154A and 154B and positioning the protrusions 154A and 154B in the cylindrical space, the pulley may be supported by the insertion portion 10 to be rotatable about the axis X1. In a state in which the pulley 152 is rotatably supported by the insertion portion 10, the pair of through-holes 151 and the shaft hole 153 are in a positional relationship of coaxial or approximately coaxial.

Figure 6:
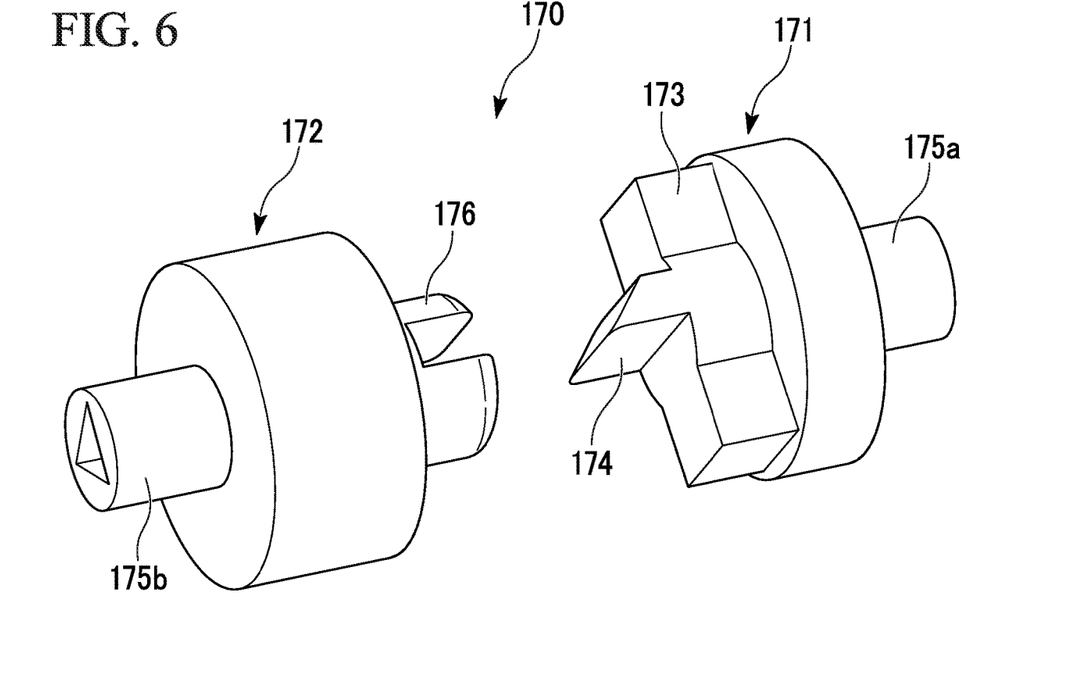
FIG. 6 is a view showing a first member and a second member constituting a cutting member in the endoscope according to the second embodiment.

A first member and a second member constituting a cutting member are disposed on both sides of the pulley 152 in the direction of the rotation axis X1. FIG. 6 shows a first member 171 and a second member 172. The first member 171 and the second member 172 constitute a cutting member 170 of the second embodiment. The first member 171 is disposed on a side on which the protrusions 154A and 154B are provided. A fitting portion 173 and a blade portion 174 are provided on a surface of the first member 171 facing the pulley 152. The fitting portion 173 can be fitted in a space between the protrusion 154A and the protrusion 154B. The blade portion 174 can protrude from the fitting portion 173 and can be inserted into the shaft hole 153. In the first member 171, a fitted portion 175a which is fitted so that the shaft portion 51a of the handle 51 does not rotate is provided on a side opposite to a side on which the fitting portion 173 is provided.

The second member 172 is disposed on a side opposite to a side on which the first member 171 is disposed. A receiving portion 176 which can be inserted into the shaft hole 153 is provided on a surface of the second member 172 facing the pulley 152. In the second member 172, like the first member 171, a fitted portion 175b is provided on a side opposite to a side on which receiving portion 176 is provided.

The first member 171 is accommodated in, for example, the above-described cylindrical space in a state in which the fitting portion 173 is not inserted into the space between the protrusions 154A and 154B. The second member 172 may be accommodated by providing a similar cylindrical space on an opposite side, but as will be described later, since the second member is integrated with the first member 171 in the emergency state, there is no particular limitation on a specific instruction mode as long as the receiving portion 176 is held at a position at which the receiving portion can be inserted into the shaft hole 153.

An operation of the endoscope 101 according to the second embodiment configured as described above, will be described. Since the operation thereof in the normal state is the same as that of the endoscope 1 in the first embodiment except that the handle 51 is not attached at the second drive portion 150, an operation thereof when a problem occurs in the first drive portion 30 will be described.

Figure 7:
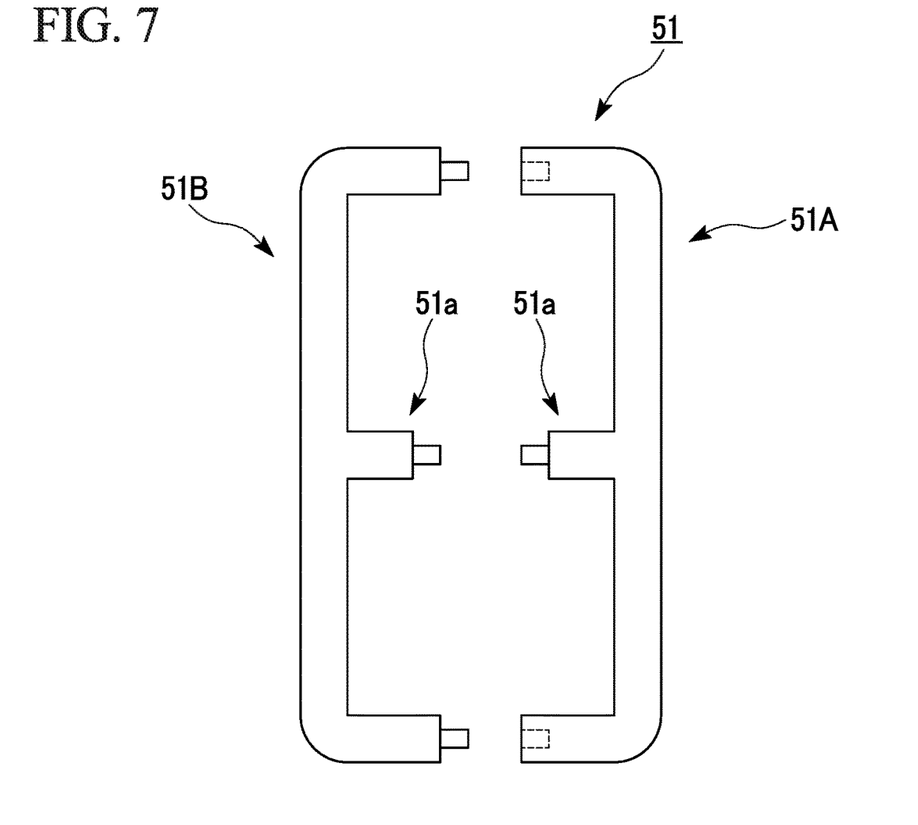
FIG. 7 is a view showing a first handle and a second handle in the endoscope according to the second embodiment.

When the problem occurs in the first drive portion 30, the user attaches the handle 51 in the pair of through-holes 151. As shown in FIG. 7, the handle 51 of the second embodiment is divided into two members including a first handle 51A and a second handle 51B, each of which has the shaft portion 51a. The user inserts the shaft portion 51a of the first handle 51A into one of the through-holes 151 and fits the shaft portion 51a to the fitted portion 175a of the first member 171. Subsequently, the user inserts the shaft portion 51a of the second handle 51B into the other one of the through-holes 151 and fits the shaft portion 51a to the fitted portion 175b of the second member 172.

The user rotates the first handle 51A around the shaft portion 51a while slightly pushing the first handle 51A toward the pulley 152 and matches phases of the pulley 152 and the first member 171 such that the fitting portion 173 can be inserted between the protrusion 154A and the protrusion 154B. When the phase matching between the pulley 152 and the first member 171 is completed, the user rotates the second handle 51B around the shaft portion 51a so that the first handle 51A and the second handle 51B are in a positional relationship in which the first handle 51A and the second handle 51B are integrally connectable, as shown in FIG. 7. The shape of the fitted portion 175a provided in the first member 171 and the shape of the fitted portion 175b provided in the second member 172 are set as follows. When the first handle 51A fitted to the first member 171 and the second handle 51B fitted to the second member 172 are in the integrally connectable positional relationship, the shapes of the fitted portion 175a and the fitted portion 175b are set such that the blade portion 174 is in a positional relationship in which the blade portion can be inserted into the receiving portion 176.

The user strongly pushes the first handle 51A toward the pulley 152 while supporting the second handle 51B in a state in which the first handle 51A and the second handle 51B are in the integrally connectable positional relationship. Then, the fitting portion 173 is inserted between the protrusion 154A and the protrusion 154B, and the blade portion 174 is inserted into the shaft hole 153 and comes in contact with the wires 61 and 62 traversing the shaft hole 153. Along with this operation, the receiving portion 176 of the second member is also inserted into the shaft hole 153. A shearing force acts on the wires 61 and 62 interposed between the blade portion 174 and the receiving portion 176, and the wires 61 and 62 are cut. When the wires 61 and 62 are cut, the first handle 51A and the second handle 51B become closer to each other and thus are integrally connectable to each other. When the first handle 51A and the second handle 51B are integrally connected, the handle 51 used in an emergency operation is completed.

After the handle 51 is completed, the bending operation of the bending portion 11 can be manually performed using the handle 51, like in the first embodiment. The first member 171 and the pulley 152 do not rotate relative to each other about the rotation axis X1 because the fitting portion 173 is fitted between the protrusions 154A and 154B. Therefore, when the handle 51 rotates, the first member 171 and the pulley 152 rotate integrally. The second member 172 also rotates together with the pulley 152 due to the fitting of the blade portion 174 and the receiving portion 176 and the connection between the first handle 51A and the second handle 51B.

As described above, according to the endoscope 101 of the second embodiment, like the endoscope 1 of the first embodiment, even when the problem occurs in the first drive portion 30 and the operation of the bending portion 11 by the first drive portion 30 becomes difficult, the wires 61 and 62 can be cut by the cutting member 170, and the bending portion 11 can be operated to be bent using the second drive portion 150.

In addition, since the cutting member 170 includes the first member 171 and the second member 172 which can fit the handle 51, the user can cut the wires 61 and 62 through a natural operation of attaching the handle 51 which is used in the emergency state. Therefore, inconvenience of the operation in the emergency state is reduced. Furthermore, since the handle 51 is attached only in the emergency state, the handle does not rotate in a follow-up manner in the normal state, and thus the user does not feel inconvenience from this.

Further, portions of the wires 61 and 62 to be cut are disposed to traverse the shaft hole 153 formed in the pulley 152. Therefore, the wire is cut by inserting the blade portion 174 and the receiving portion 176 of the cutting member 170 into the shaft hole 153, and the first member 171 and the second member 172 are attached to be coaxial with the pulley 152. Therefore, when the handle 51 attached at the cutting member 170 is operated after the cutting of the wires 61 and 62, rotation of the handle 51 is suitably transmitted to the pulley 152 via the cutting member 170, and thus switching to the manual operation in the emergency state can be smoothly performed.

In addition, the blade portion 174 and the receiving portion 176 are set to be in a suitable positional relationship when the first handle 51A and the second handle 51B which are fitted to the first member 171 and the second member 172 are in the integrally connectable positional relationship. Therefore, the user can intuitively position the first member 171 and the second member 172 in a positional relationship in which the wire can be cut by adjusting positions of the first handle 51A and the second handle 51B in a state in which the fitting portion 173 is fitted between the protrusions 154A and 154B.

In the above description, the fitting portion 173 of the first member 171 is disposed so as not to be inserted between the protrusions 154A and 154B in the normal state. However, the fitting portion 173 may be slightly inserted between the protrusions 154A and 154B within an extent in which the blade portion 174 is not in contact with the wire in advance. Accordingly, positioning of the fitting portion 173 may be unnecessary, and the operation in the emergency state may be further simplified.

If inconvenience in the normal state is not a concern, the handle may be fitted to the first member and the second member in advance and then may be rotated in the follow-up manner in the normal state.

Next, a third embodiment will be described with reference to FIGS. 8 and 9. The third embodiment is different from each of the above-described first and second embodiments in that the wire is not cut in the emergency state.

Figure 8:
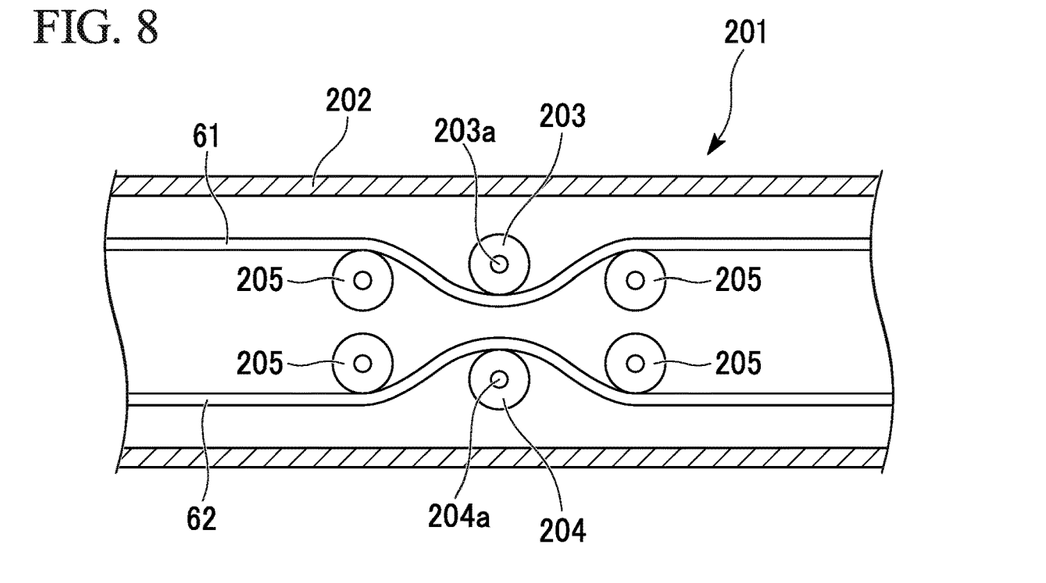
FIG. 8 is a cross-sectional view showing an insertion portion of an endoscope according to a third embodiment.

FIG. 8 is a partial cross-sectional view of an insertion portion 202 of an endoscope 201 according to the third embodiment. A portion shown in FIG. 8 is a portion between the first drive portion 30 and the second drive portion 50 (neither of which is shown). A pair of idler pulleys (transmission blocking devices) 203 and 204 are rotatably attached between the first drive portion 30 and the second drive portion 50. The wires 61 and 62 are tensioned to approach each other at positions of the idler pulleys 203 and 204 by the idler pulleys 203 and 204 and the four fixed pulleys 205, and a path thereof is extended compared with a state in which the wires extend in parallel. The four fixed pulleys 205 are disposed with the idler pulleys 203 and 204 interposed therebetween. The length of the extended path is secured to be longer than an advancing/retracting stroke of the wires 61 and 62 in the endoscope 201 and may be, for example, 20 mm or more.

In the endoscope 201, the wires 61 and 62 are advanced and retracted by the first drive portion 30 in a state in which the path is extended by the idler pulleys 203 and 204 in a normal state. When the problem occurs in the first drive portion 30, the user moves the idler pulleys 203 and 204 away from each other, instead of cutting the wires 61 and 62. A mechanism for moving the idler pulleys is not particularly limited and may be appropriately configured, for example, to pull a lever connected to a shaft 203a of the idler pulley 203 and a shaft 204a of the idler pulley 204.

Figure 9:
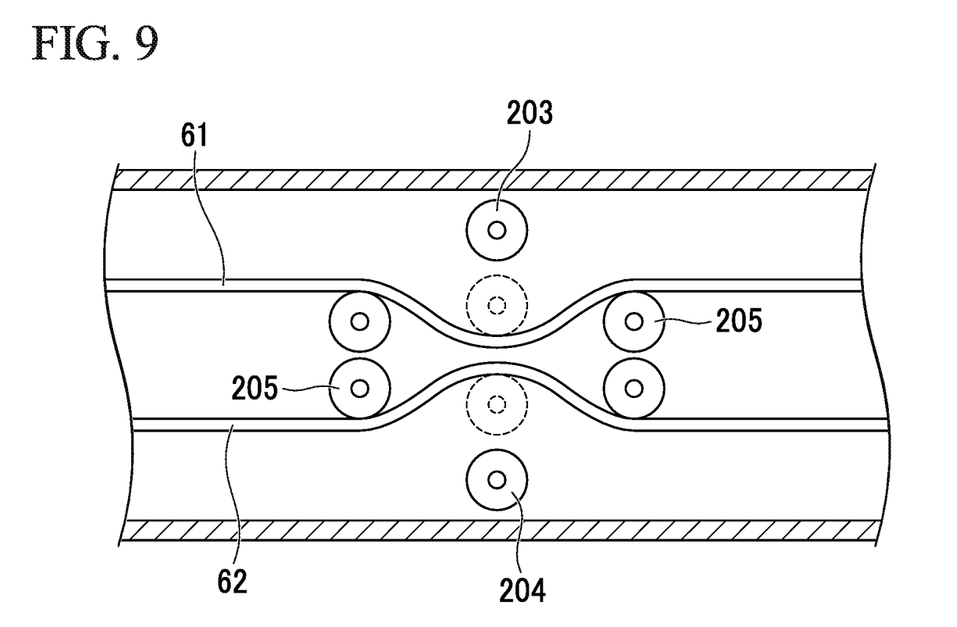
FIG. 9 is a partial cross-sectional view showing the insertion portion of the endoscope according to the third embodiment in an emergency state.

When the idler pulleys 203 and 204 are moved, the wires 61 and 62 are loosened and are not supported by the idler pulleys 203 and 204, as shown in FIG. 9. As a result, the wires 61 and 62 are loosened on a proximal end side from the second drive portion 50, and power transmission from the first drive portion 30 to the wires 61 and 62 is blocked.

As in the first embodiment, the user can perform the bending operation of the bending portion 11 by inputting an operation to the second drive portion 50 using the handle 51. The wires 61 and 62 between the first drive portion 30 and the second drive portion 50 are pushed and pulled with the operation of the second drive portion 50. However, since the wires 61 and 62 are loosened beyond the stroke by movement of the idler pulleys 203 and 204, the operation is not hindered by pulling or the like due to the operation of the second drive portion 50.

As described above, according to the endoscope 201 of the third embodiment, like the endoscope 1 of the first embodiment, even when the problem occurs in the first drive portion 30 and the operation of the bending portion 11 by the first drive portion 30 becomes difficult, the bending operation of the bending portion 11 can be performed using the second drive portion 50.

Since the wires 61 and 62 are not cut, the wires 61 and 62 can be easily put in a usable state after completion of the procedure by adjusting a tension of the wires or the like. Therefore, the configuration of the third embodiment is suitable for repeated use of a medical manipulator by performing sterilization or the like after use.

In the third embodiment, an example in which the length of the path of the wires 61 and 62 is extended using the idler pulleys 203 and 204 has been described. Alternatively, the length of the path of the wires may be extended by a pin or the like inserted into the insertion portion. In this case, the wires can be loosened by simply pulling out the pin in the emergency state, and thus a structure can be simplified. In the case of using the pin or the like, frictional resistance of the wire may be reduced by coating or the like on an outer circumferential surface thereof.

Embodiments have been described above, but the technical scope is not limited to the above-described embodiments, and various combinations of elements may be changed or various modifications of each of the elements may be added or deleted without departing from the spirit of the present invention.

For example, the endoscope serving as the medical manipulator is not limited to the insertion portion formed of a rigid material. Therefore, a flexible endoscope having a flexible insertion portion may be used as long as the bending portion is driven by a drive mechanism such as a motor in the normal state.

In the above description, an example in which the bending portion has a pair of wires and is bent in the two directions has been described, but two pairs of wires may be provided so that the bending portion can be bent in four directions.

The end effector of the medical manipulator is not limited to the above-described observation portion. For example, various configurations used for treatment, such as a high-frequency knife used while an electric current is applied or a grasping forceps used while the electric current is not applied, may be used.

Although preferred embodiments have been described above, the present invention is not limited to the embodiments and modifications thereof. Additions, omissions, substitutions and other changes in the structure are possible without departing from the spirit of the present invention. The present invention is not limited by the foregoing description but is limited only by the scope of the appended claims.

What is claimed is:

1. A medical manipulator comprising:
   an insertion portion comprising a bending portion;
   an actuator configured to generate a first drive force for moving the bending portion;
   a lever configured to generate a second drive force for moving the bending portion, the lever being used to move the bending portion instead of the actuator;
   a wire configured to transmit the first drive force or the second drive force to the bending portion; and
   a transmission blocking device configured to switch a drive force transmitted by the wire from the first drive force to the second drive force, the transmission blocking device being configured to produce slack in a portion of the wire between the actuator and the lever.

2. The medical manipulator according to claim 1, wherein the lever comprises a handle configured to generate the second drive force when the handle is moved from a first position to a second position.

3. The medical manipulator according to claim 1, wherein the transmission blocking device comprises a first pulley configured to be moved so as to produce the slack in the portion of the wire between the actuator and the lever.

4. The medical manipulator according to claim 3, wherein the transmission blocking device further comprises a plurality of second pulleys arranged to sandwich the first pulley, the plurality of second pulleys being configured to support the wire outside of the portion of the wire being slacked.

5. The medical manipulator according to claim 3, wherein the first pulley being configured to be moved so as to press the wire from a direction substantially perpendicular to the longitudinal direction of the wire.

6. A medical manipulator comprising:
   an insertion portion comprising a joint;
   a wire configured to connect to the joint;
   an actuator configured to be connected to a proximal end of the wire, the actuator being configured to generate a first force to bend the joint;
   a drive pulley configured to be connected to the wire at a first longitudinal position of the wire, the drive pulley being configured to generate a second force to bend the joint;
   a tensioner connected to the wire to change the tension applied to the wire, the tensioner being arranged at a second longitudinal position of the wire, the second longitudinal position being between the drive pulley and the actuator;
   wherein the joint is bent by the first force when the tensioner is in a first position that tensions the wire to a first tension and the joint is bent by the second force when the tensioner is in a second position that slackens the wire to a second tension less than the first tension
   wherein the tensioner is configured to move between the first position and the second position.

7. The medical manipulator according to claim 6, wherein the drive pulley comprising a shaft hole, a shaft is inserted into the shaft hole, the drive pulley being rotated about the shaft by the second force.

8. The medical manipulator according to claim 7, wherein the tensioner is one or more tensioner pulleys.

9. The medical manipulator according to claim 8, wherein the one or more tensioner pulleys are configured to move from the first position to the second position.

10. The medical manipulator according to claim 7, wherein the shaft is connected to a handle for inputting the second force.

11. The medical manipulator according to claim 6, further comprising one or more idler pulleys, the one or more idler pulleys being configured to support the wire when the wire is in the first position.

12. The medical manipulator according to claim 11, wherein
   the one or more idler pulleys comprises a first idler pulley and a second idler pulley, and
   the first idler pulley is located proximal to the tensioner pulley, and the second idler pulley is located distally to the tensioner pulley.

13. The medical manipulator according to claim 12, wherein the one or more idler pulleys are located radially inward relative to the wire, and the one or more tensioner pulleys are located radially outward relative to the wire when the tensioner is in the second position.

14. The medical manipulator according to claim 6, wherein the driver pulley comprises a protrusion, the wire being connected to the protrusion.

15. The medical manipulator according to claim 14, wherein the wire is wound around the protrusion.

* * * * *